United States Patent [19]

McGee

[11] Patent Number: 4,878,749
[45] Date of Patent: Nov. 7, 1989

[54] PROTECTIVE EYEWEAR WITH INTERCHANGEABLE DECORATIVE FRAMES

[76] Inventor: James E. McGee, 31635 Blue Meadow La., Westlake Village, Calif. 91361

[21] Appl. No.: 212,881

[22] Filed: Jun. 29, 1988

[51] Int. Cl.$^4$ .............................................. G02C 11/02
[52] U.S. Cl. ...................................... 351/52; 351/158; 351/116
[58] Field of Search ...................... 351/51, 52, 47, 158, 351/114, 115, 116; 2/429, 433

[56] References Cited

U.S. PATENT DOCUMENTS

| | | | |
|---|---|---|---|
| D. 289,301 | 4/1987 | Jannard | D16/112 |
| D. 293,450 | 12/1987 | Jannard | D16/102 |
| D. 294,833 | 3/1988 | Holden | D16/112 |
| 2,210,507 | 8/1940 | Spill | 351/116 |
| 4,070,103 | 1/1978 | Meeker | 351/52 |
| 4,674,851 | 6/1987 | Jannard | 351/47 |

Primary Examiner—Rodney B. Bovernick
Assistant Examiner—P. M. Dzierzynski
Attorney, Agent, or Firm—David O'Reilly

[57] ABSTRACT

Protective eyewear which may be tinted for use as sunglasses having a preformed one piece lens arrangement with a recessed border and removable temples hinged to the preformed lens. The removable temple pieces have posts which fit sockets at opposite upper and lower ends of the preformed lens. Interchangeable decorative frames allow the wearer to change the appearance of the protective eyewear at will. The interchangeable decorative frames have pins which snap into the sockets used for the hinges for the temple pieces allowing the frame to be easily removed and replaced with a different color or design decorative frame.

2 Claims, 1 Drawing Sheet

PROTECTIVE EYEWEAR WITH INTERCHANGEABLE DECORATIVE FRAMES

FIELD OF THE INVENTION his invention relates to protective eyewear, and more particularly relates to protective eyewear having interchangeable decorative frames which can be easily removed and exchanged.

BACKGROUND OF THE INVENTION

There are a variety of protective eyewear now made of durable attractive synthetic materials. This protective eyewear can be worn for sporting events, hazardous working conditions or in any place where protection of the eyes from injury is desirable. The protective eyewear is usually tinted for use as sunglasses and the most frequent use of these lightweight durable glasses is for participation in sporting events, such as skiing.

Because of the nature of these types of glasses they are made of a highly durable plastic material and come in a wide variety of designs. Sportsmen and sportswomen who wear these protective eyewear are often very fashion conscious and would find different designs desirable for different purposes, and a wide variety of circumstances. However, owning and carrying a number of pairs of this protective eyewear is not practical. Therefore, it would be advantageous if a single pair of protective eyewear could be attractively decorated to provide a wide variety of designs.

There are sunglasses known that have a frame and nosepiece construction that permits them to be removed and replaced as well as allowing pane replacement. These glasses are disclosed and described in U.S. Pat. No. 4,674,851, issued June 23, 1987. In these glasses, however, the frame and temples remain the same but the pane, lens and nosepiece can be removed and replaced. They do not permit or describe any type of interchangeable decorative frame.

It is therefore one object of the present invention to provide protective eyewear that can be changed to provide a wide variety of designs.

Yet another object of the present invention is to provide protective eyewear that can be selectively changed to provide a different appearing frame.

Still another object of the present invention is to provide protective eyewear having interchangeable decorative frames that can be easily removed and exchanged.

Still another object of the present invention is to provide eyewear having removeable temple pieces and decorative removeable frames that are mounted on the same socket.

BRIEF DESCRIPTION OF THE INVENTION

The purpose of the present invention is to provide protective eyewear having interchangeable decorative frames which allows the appearance of the glasses to be quickly and easily altered. The protective eyewear can be tinted or clear and are designed to be worn with or without regular eyewear.

The protective eyewear pane or lens are constructed with an integrally formed frame having surfaces for receiving and retaining a snap-on decorative frame. The snap-on decorative frame allows the wearer to mix and match the eyeglasses to meet todays fashions.

The eyewear is comprised of a preformed lens and nose rest arrangement having a flanged border for mounting the interchangeable fashion frames. The flanged border is integrally formed adjacent each temple portion of the lens and nose rest and includes sockets for mounting the temple pieces or arms. The sockets receive pins mounted on the lower and upper extremities of the temple pieces forming a hinge to allow the temple pieces to be folded.

The interchangeable decorative frame is comprised of a bar fitting on and spanning the top of the preformed lens having side pieces of flanges that conform to the shape of the lens. These interchangeable decorative frames can be produced in a wide variety of colors and shapes. They are installed by simply slipping the decorative frame around the lens and have tabs or pins engaging sockets to retain the decorative frame on the preformed lens.

The above and other novel features and advantages of this invention will be fully understood from the following detailed description and the accompanying drawings, in which:

DETAILED DESCRIPTION OF THE INVENTION

Figure 1:
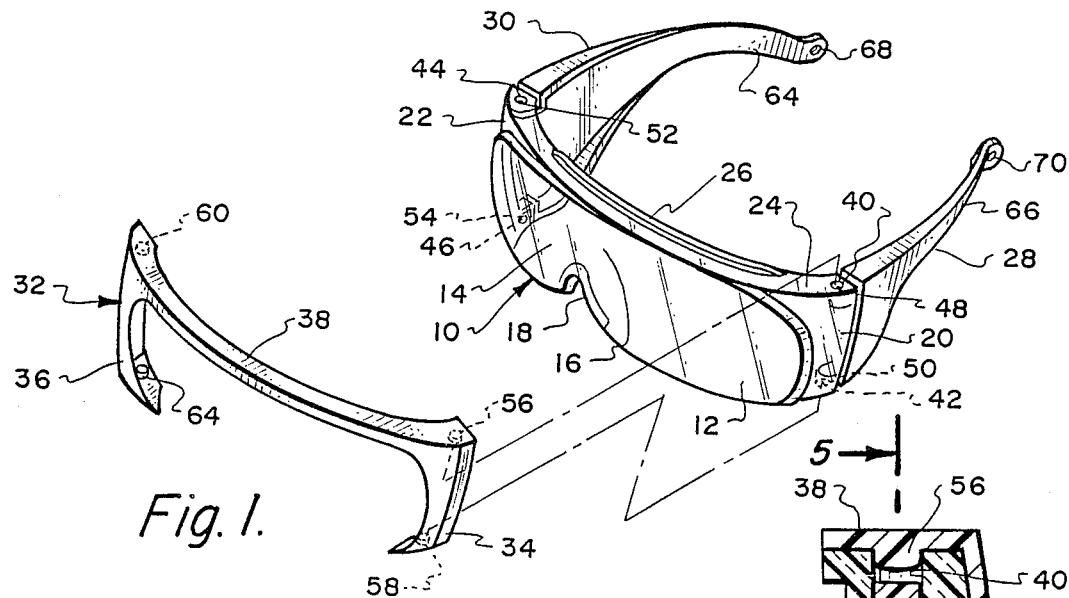
FIG. 1 is an exploded perspective view of protective eyewear and an interchangeable decorative frame according to the invention.

The protective eyewear which may be tinted for use as sunglasses are shown generally in FIG. 1, in which a contoured molded single planar piece 10 forms lenses 12 and 14, joined by a bridge portion 16 above nose rest 18. The preformed transparent lens portions 12 and 14, are surrounded by recessed portions 20 and 22 at each end and a flange or skirt 24 along the top or eyebrow portion forming a frame. Rib 26 along the upper portion of the upper edge of skirt 24 acts as an alignment or positioning rib, as will be described in greater detail hereinafter.

Rearward extending arms 28 and 30 form temple pieces for holding the protective eyewear on the wearers head. Temples 28 and 30 are removably attached to the frame integrally formed on the planar piece 10 for easy replacement if broken or damaged. The hinges allow the temple pieces to be folded away when the protective eyewear or sunglasses are carried in a case.

Figure 2:
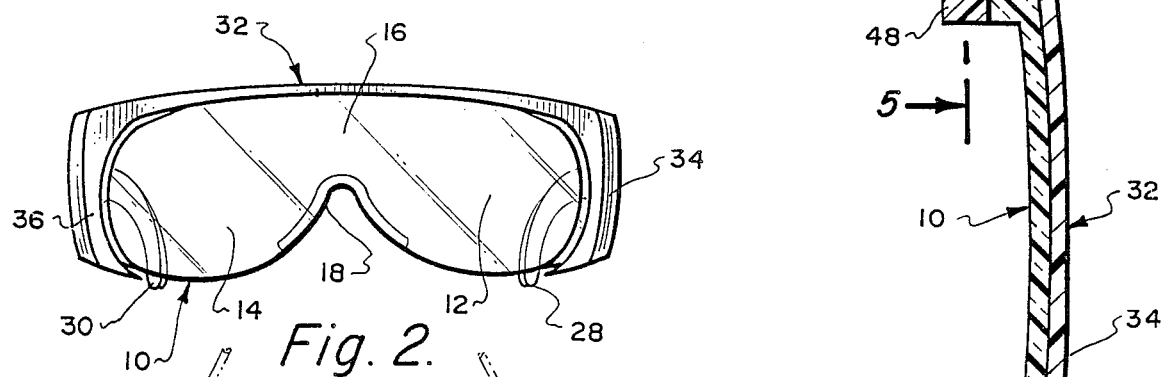
FIG. 2 is a front elevation of the protective eyewear with the decorative interchangeable frame installed.

An interchangeable decorative frame 32 mounts over the frame formed on the planar piece comprised of recessed flanges or portions 20 and 22 and skirt 24. The interchangeable frame is comprised of lateral lens framing pieces 34 and 36 joined by bar 38. Interchangeable frame 32 is mounted on the eyewear with bar 38 resting on skirt 24 and lateral end pieces 34 and 36 mating with flanges 20 and 22 surrounding lenses 12 and 14 as illustrated in FIG. 2. Rib 26 acts as a guide to properly position interchangeable frame 32 on the eyewear.

Figure 3:
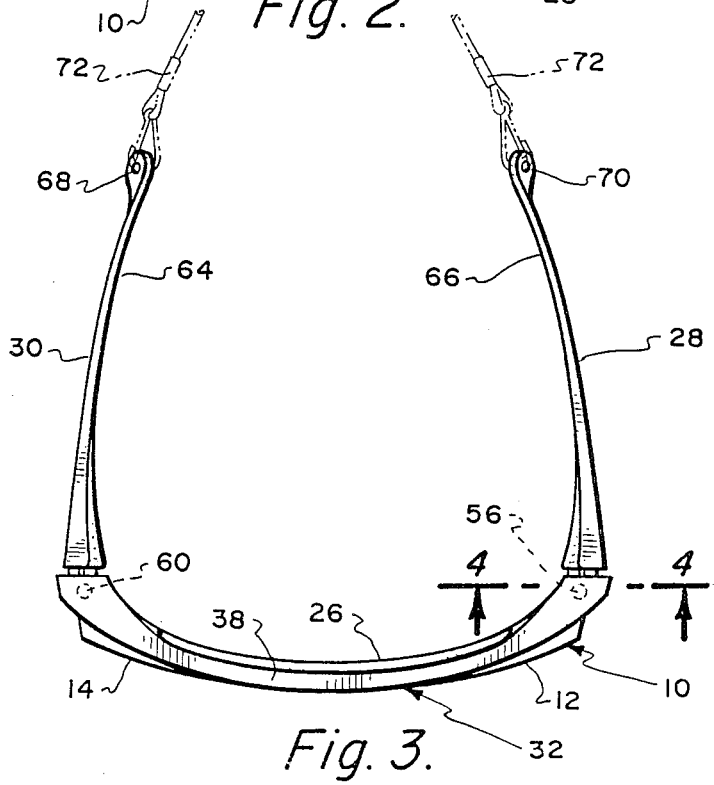
FIG. 3 is a top view of the protective eyewear with the decorative interchangeable frames installed.
Figure 4:
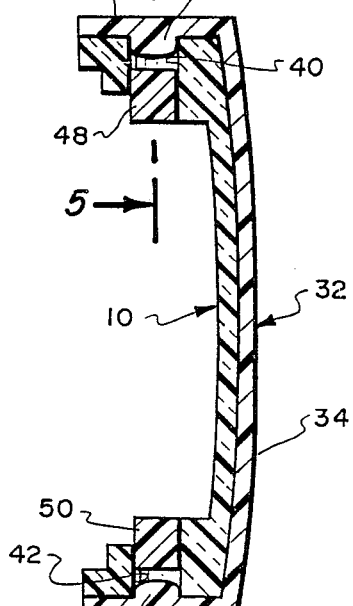
FIG. 4 is a sectional view taken at 4—4 of FIG. 3.
Figure 5:
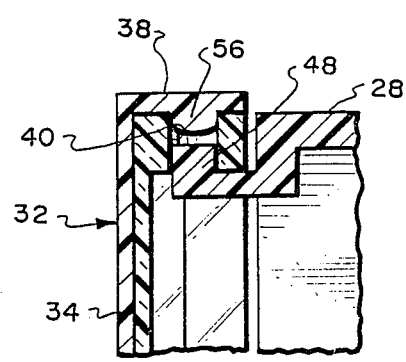
FIG. 5 is a sectional view taken at 5—5 of FIG. 4.

Interchangeable frame 32 is secured on the eyewear by using the mechanical coupling forming the hinge for temple pieces 28 and 30 as shown in FIGS. 3 through 5. Sockets are formed by holes 40, 42, 44 and 46 in the upper and lower outer end portions of planar piece 10.

These holes provide sockets for receiving posts 48 and 50 formed on temple 28. Temple 30 has similar posts 52 and 54. The mechanical coupling of posts 48 and 50, and sockets 40 and 42 form a hinge for temple 28. Additionally, posts 48 and 50 are made short or shallow enough 26 to allow holes 40 and 42 to act as sockets for mounting interchangeable frame 32.

Peripheral skirted portion of interchangeable frame 32 is formed with pins 56, 58, 60 and 62 as shown in FIG. 1. Interchangeable frame 32 is mounted by positioning bar 38 on skirt 24 against rib 26 and forcing pins 56, 58, 60 and 62 into the respective sockets formed by holes 40, 42, 44 and 46. In this manner the interchangeable frame is retained on the protective eyewear. Bar 38 is sufficiently flexible that these pins can be easily dislodged from the sockets for removal of and replacement with another interchangeable decorative frame of different color or design.

Right and left temple pieces 28 and 30 are easily removed by applying a force at the upper and lower portion of the temple (i.e. squeezing) to dislodge either posts 48 or 50 from the socket allowing the temple to be removed. A new temple is replaced by simply reversing the procedure by fitting one of the posts into the socket and squeezing the flexible temple to engage the other posts with the opposite socket.

It should be understood that the planar piece forming lenses 12 and 14 recessed flanges 20 and 22, and skirt 24 is contoured to fit the shape of the face and is somewhat enlarged to fit over existing eyeglasses. Additionally, temples 28 and 30 have an exaggerated curvature at 64 and 66 to press firmly against the side of the head. This curvature of the the temples allow the width of the planar piece forming lenses 12 and 14 and the frame to be substantially larger than the width of normal eyeglasses, allowing this protective eyewear to be worn with existing glasses. Holes 68 and 70 at the outer ends of temples 28 and 30, allow a leash or retaining cord 72, shown in phantom lines in FIG. 3, to be easily clipped to the ends of the temples when these protective eyeglasses are worn.

Thus there has been described protective eyewear having removable interchangeable decorative frames to allow mixing and matching the frames with todays fashions. Preferably the lenses are integrally formed with the planar piece and are of optical quality having a tint which will block normal ultraviolet rays. The glass design includes an easily attached eyeglass retaining cord that can be quickly and easily clipped to the end of the temples. The interchangeable frame though shown as having post-fitting sockets used to provide the mechanical linkage for hinges for the temples, can be mounted in other ways if desired. Instead of posts, clips could be provided on the rear upper and lower edges of the interchangeable frame to engage and secure the frame to the eyeglasses.

This invention is not to be limited by the embodiment shown in the drawings and described in the description which is given by way of example and not of limitation, but only in accordance with the scope of the appended claims.

What is claimed is;

1. Protective eyewear with interchangeable decorative frames comprising:
   preformed lens having a recessed border forming a frame;
   right and left temple pieces on said preformed lens;
   hinge means securing said temple pieces to said preformed lens;
   said hinge means comprising posts formed on said temple pieces and hinge sockets formed on said preformed lens, said posts on said temple pieces constructed to snap into said hinge sockets on said preformed lens;
   an interchangeable decorative frame fitting said recessed border around said preformed lens;
   means detachably securing said interchangeable decorative frame to said preformed lens;
   said means detachably securing said interchangeable decorative frame comprising posts formed on said decorative frame and sockets formed on each end of said preformed lens; said posts on said interchangeable decorative frame constructed to snap into said sockets formed in said preformed lens;
   said hinge sockets and said sockets for mounting said interchangeable decorative frame being the same sockets;
   whereby said hinge sockets support both said temple pieces and said interchangeable frame so that said temple pieces and said interchangeable decorative frame may be easily removed and replaced to change the appearance of said protective eyewear.

2. The protective eyewear according to claim 1 including aligment means for aligning said interchangeable decorative frame on said preformed lens; said alignment means comprising a rib traversing an upper surface of said preformed lens for abutting said interchangeable decorative frame.

* * * * *